United States Patent
Altuev et al.

(10) Patent No.: US 11,482,031 B2
(45) Date of Patent: Oct. 25, 2022

(54) SYSTEM AND METHOD FOR DETECTING POTENTIALLY DANGEROUS HUMAN POSTURE

(71) Applicant: OOO ITV Group, Moscow (RU)

(72) Inventors: Murat Kazievich Altuev, Moscow (RU); Egor Petrovich Suchkov, Tuapse (RU); Egor Yurevich Lvov, Moscow (RU)

(73) Assignee: OOO ITV Group, Moscow (RU)

( * ) Notice: Subject to any disclaimer, the term of this patent is extended or adjusted under 35 U.S.C. 154(b) by 68 days.

(21) Appl. No.: 16/931,570

(22) Filed: Jul. 17, 2020

(65) Prior Publication Data

US 2021/0019508 A1  Jan. 21, 2021

(51) Int. Cl.
| | |
|---|---|
| *A61B 5/11* | (2006.01) |
| *G06V 40/10* | (2022.01) |
| *G08B 21/02* | (2006.01) |
| *G06V 20/00* | (2022.01) |
| *G06V 20/40* | (2022.01) |
| *G06V 20/52* | (2022.01) |

(52) U.S. Cl.
CPC .......... *G06V 40/103* (2022.01); *A61B 5/1116* (2013.01); *A61B 5/1117* (2013.01); *G06V 20/35* (2022.01); *G06V 20/49* (2022.01); *G06V 20/52* (2022.01); *G08B 21/0297* (2013.01); *G06T 2207/30196* (2013.01)

(58) Field of Classification Search
CPC .......... G06K 9/00369; G06K 9/00684; G06K 9/00765; G06K 9/00771; G08B 21/0297; A61B 5/1116; A61B 5/1117; G06T 2207/30196
See application file for complete search history.

(56) References Cited

U.S. PATENT DOCUMENTS

2014/0066811 A1 * 3/2014 Garney ................ A61B 5/1128
600/587

* cited by examiner

*Primary Examiner* — Kenny A Cese
(74) *Attorney, Agent, or Firm* — Ilya R. Lapshin; IRL Legal Services, LLC

(57) ABSTRACT

The invention refers to the field of processing and analyzing video data received from video surveillance cameras, and more specifically, to technologies aimed at detecting a human in a frame and at analyzing their posture for subsequent detection of potentially dangerous situations by video data. The system for detecting potentially dangerous situations contains video cameras, a memory, a graphical user interface (GUI), and a data processing device. Data processing device is configured to receive real-time video data, analyze the received video data, obtain horizontal lines for each of the set corrective vertical lines, split the frame into zones, construct the leg vector based on a pair of the lower limbs key points and determine their belonging to one of the resulting zones, construct a back vector, determine the lower limbs tilt angle between the resulting back vector and the leg vector, determine the human's posture, and detect a potentially dangerous situation, if the human's posture is one of the postures indicating a potentially dangerous situation.

33 Claims, 2 Drawing Sheets

SYSTEM AND METHOD FOR DETECTING POTENTIALLY DANGEROUS HUMAN POSTURE

RELATED APPLICATIONS

This application claims priority to Russian Patent Application No. RU 2019122732, filed Jul. 18, 2019, which is incorporated herein by reference in its entirety.

FIELD OF THE INVENTION

The invention relates to the field of processing and analyzing video data received from video surveillance cameras, and more specifically, to technologies aimed at detecting a person in a frame and at analyzing their posture for subsequent detection of potentially dangerous situations by video data.

BACKGROUND

Surveillance systems are used to protect buildings or territories. Usually these systems use multiple cameras to monitor the protected area. Video data received from the video surveillance cameras allow the operator of the security system to assess the situation occurring in the protected area and to respond timely in case of detection of a dangerous situation.

When monitoring a very large area, it is difficult for the system operator to notice a dangerous situation without a computer timely analysis of the video content and to organize a timely security service response (due to the large flow of information that should be timely viewed). There is a high probability of missing a violation in a protected area due to a prolonged concentration of attention on another protected zone (the human factor).

Modern video surveillance systems (VSS) are based on image processing and pattern recognition algorithms that allow video analysis without a direct involvement of a person. The video surveillance systems, depending on their specific targets, can implement many functions, such as: object detection, object identification or recognition, object posture or gesture analysis, object trajectory analysis, and many others.

Recently, technologies for determining person's posture from video data (e.g. EP2843621A1, U.S. Pat. No. 7,340,100B2, US2016/0217326A1, and CN106203363A) have become very popular.

Personal posture evaluation refers to computer vision techniques that detect humans in images or video frames. Then the person's skeleton is detected, and the positions of all limbs are determined and recorded. This technique can be used in different fields of technology, such as augmented reality technologies (US2016/0085310A1). In addition, the personal gesture and posture recognition is used to determine the reaction to goods or services seen in stores or viewed on web pages in a browser.

The concept is in the use of human posture determination technology for detecting potentially dangerous situations using video data to respond in a timely manner. The main task of the technical solutions is to ensure correct detection of potentially dangerous situations using video data and to respond quickly once it has been detected.

One known disclosure is provided in the US patent application publication US2016/0314666 A1, published Oct. 27, 2016, which describes systems and methods for detecting personal distress and gesture commands in security video. The methods include receiving a sequence of images from a video device monitoring a secured area, analyzing the sequence of images to detect a presence of a human in the sequence of images, when the presence of the human is detected in the sequence of images, analyzing the sequence of images to detect one of a plurality of contexts that requires action in the sequence of images, and when the one of the plurality of contexts that requires the action is detected in the sequence of images, transmitting a signal to execute the action. Each of the plurality of contexts can include an act performed by the human or a condition of the human irrespective of the human being in motion or being stationary.

The main difference of this disclosure from the present disclosure consists in absence of a detailed description of the algorithm for determining the person's posture and, accordingly, the situations that require the response.

Another disclosure known in the art is provided in the US patent publication U.S. Pat. No. 7,613,324B2, published Nov. 3, 2009, which describes detecting a change in a posture of a person shown in the video data by receiving input video data; detecting a target in the video data; tracking the target; identifying a target as a human; and detecting a change in a posture of the human target in the video data when a change in at least one of a height or aspect ratio of the human target exceeds a predetermined threshold by determining the height or the aspect ratio of the target in a first frame of the video data; determining the height or aspect ratio of the target in a second frame of the video data; calculating a difference between the height or aspect ratio of the target in the first and second frames; detecting the change in the posture when either difference exceeds a predetermined threshold; determining an elapsed time between the first and second frames; and detecting the change in the posture when the elapsed time is below a predetermined threshold.

The main difference between this disclosure and the present disclosure consists in significant difference in the algorithms for determining the person's posture. In addition, the known disclosure specializes only in detection of a person's falling or getting up using video data.

BRIEF SUMMARY

This technical solution is aimed to eliminate the disadvantages of the previous background of the invention and develop the existing solutions.

The technical result of the claimed group of inventions is improved accuracy of identifying potentially dangerous situations by analyzing the human posture found in the video data.

This technical result is achieved by the fact that the system for detecting potentially dangerous situations contain of the following components: at least one video camera; data storage with video data storage function; graphical user interface (GUI); at least one data processing device configured for: real-time receipt of video data from at least one video camera; analysis of the received video data for detecting at least one human in the frame and receiving the key points of their skeleton, whereby, after receiving key points, the user sets at least three corrective vertical lines per frame with a height equal to the average human height and parallel to the assumed vector of the back formed by the resulting key points using the GUI, whereby the mentioned vertical lines located on the same underlying plane as the mentioned human; receiving horizontal lines for each of the specified corrective vertical lines; splitting the frame into zones based on preset corrective vertical lines for determining the vertical lines that are the closest to the human; constructing at least one leg vector based on a pair of the lower limbs key points and determining their (i.e. points') belonging to one of the resulting zones; constructing a back's vector based on the vertical lines that formed the resulting zone and based on the resulting horizontal lines; determination of the lower limbs tilt angle between the resulting back vector and leg vector; determination of the human's posture based on comparison of the resulting lower limbs tilt angle with a preset threshold; identification of a potentially dangerous situation if the human's posture is one of the postures indicating a potentially dangerous situation.

This technical result is also achieved by the method of detecting potentially dangerous situations implemented by at least one data processing device, whereby the method contains the stages, at which the following events happen: real-time video data is received from at least one video camera; video data is analyzed for detecting at least one human in the frame and receiving the key points of their skeleton, whereby, after receiving the key points, the user sets at least three corrective vertical lines in the frame with the height equal to the average human height and parallel to the assumed back vector formed by the resulting key points using the GUI, whereby the mentioned vertical lines are located on the same underlying plane as the human mentioned; the horizontal lines for each of the set corrective vertical lines are constructed; the frame is split into zones based on preset corrective vertical lines for determining the corrective vertical lines that are closest to the human; at least one leg vector is formed based on a pair of the lower limbs key points and their belonging to one of the resulting zones is determined; the back vector is constructed on the basis of vertical lines that formed the resulting zone and on the basis of horizontal lines; the lower limbs tilt angle between the resulting back vector and the leg vector is determined; the human's posture is determined based on comparison of the resulting lower limbs tilt angle with preset threshold value; a potentially dangerous situation is detected if a human's posture is one of the postures indicating a potentially dangerous situation.

In one specific embodiment of the claimed solution, the following steps are performed when horizontal lines for each of the set corrective vertical lines are constructed: (a) selecting the first vertical line by passing through all the set corrective vertical lines; (b) selecting the second vertical line by passing through all the remaining lines once the first line is selected based on the set corrective vertical lines; (c) getting the equation of the line passing through the upper points of the selected vertical lines; (d) getting the equation of the line passing through the lower points of the selected vertical lines; (e) calculating the point of intersection of the mentioned lines by solving a system of linear equations; (f) repeating the steps (b)-(e) to obtain a set of points; (g) obtaining the optimal points from the resulting set of points by applying algorithm for estimating the parameters based on random samples (RANSAC); (h) obtaining a horizontal line for the first corrective vertical line based on the resulting optimal points; (i) repeating the steps (a) to (g) to obtain the horizontal lines for each of the set corrective vertical lines.

In another specific embodiment of the claimed solution, the frame is split into zones by using Delaunay triangulation method, based on the location of the corrective vertical lines in the frame.

In another specific embodiment of the claimed solution, when the leg vector is constructed, the middle of the hip is considered as one key point, implying a point between the key points of the hip, and either the point of the ankle or the point of the knee is considered as the second key point, whereby the mentioned points also imply the middle between the key points of the same name.

In another specific embodiment of the claimed solution, the human's posture indicating a potentially dangerous situation is one of the postures that characterize: a sitting human in a frame, a lying human in a frame, a human with at least one arm outstretched forward, a human with at least one arm raised.

In another specific embodiment of the claimed solution, the posture of the sitting human in the frame characterizes a person sitting either on a chair, floor, or on their hunkers.

In another specific embodiment of the claimed solution, if the mentioned lower limbs tilt angle exceeds the preset threshold, the human in the frame is considered to be either in a sitting or lying posture.

In another specific embodiment of the claimed solution, if the mentioned lower limbs tilt angle is less than the preset threshold value, whereby if the length ratio of the segment connecting the point of the middle of the lower limbs with the projection of the neck point on the back vector, to the human's height exceeds the preset second threshold, then the human in the frame is considered to be in the lying posture in the direction of the camera.

In another specific embodiment of the claimed solution, a new back vector is constructed based on the key point of the neck and the key point of the hips, whereby, if the tilt angle of this new back vector from the previously mentioned back vector exceeds the preset third threshold, then the human is in the lying posture in the frame.

In another specific embodiment of the claimed solution, at least one arm vector is constructed based on a pair of key points of the upper limbs, whereby, if the arm vector is perpendicular to the back vector, the human is considered to be in a posture with at least one arm outstretched forward.

In another specific embodiment of the claimed solution, at least one arm vector is constructed based on a pair of the upper limbs key points, whereby, if the arm vector is parallel to the back vector, and the hand key point is higher than the shoulder key point, the human is considered to be in a position with at least one hand raised.

In another specific embodiment of the claimed solution, a potentially dangerous situation is identified if a human's posture indicating a potentially dangerous situation is observed in the video data within a preset period of time.

In another specific embodiment of the claimed solution, the mentioned time is adjusted by the user when configuring the system operation.

In another specific embodiment of the claimed solution, the graphical user interface is configured to enable the user to adjust the frame perspective before starting operation of the system.

In another specific embodiment of the claimed solution, when a potentially dangerous situation is detected, the data processing device automatically performs one or more actions preset by the user.

In another specific embodiment of the claimed solution, the mentioned actions include: recording video data to the archive, exporting a frame or a video, initiating an alarm, notifying the user with SMS, notifying the user by email, notifying the user with audio.

This technical result is also achieved by a computer-readable data carrier containing instructions executed by the computer processor for implementation of ways for detecting potentially dangerous situations.

DETAILED DESCRIPTION

Description of the approximate embodiments of the claimed group of inventions is presented below. However, the claimed group of inventions is not limited only to these embodiments. It will be obvious to persons who are experienced in this field that other embodiments may fall within the scope of the claimed group of inventions described in the claim.

The claimed technical solution in its various embodiments can be implemented in the form of computer systems and methods for detecting potentially dangerous situations, as well as in the form of a computer-readable data carrier.

Figure 1:
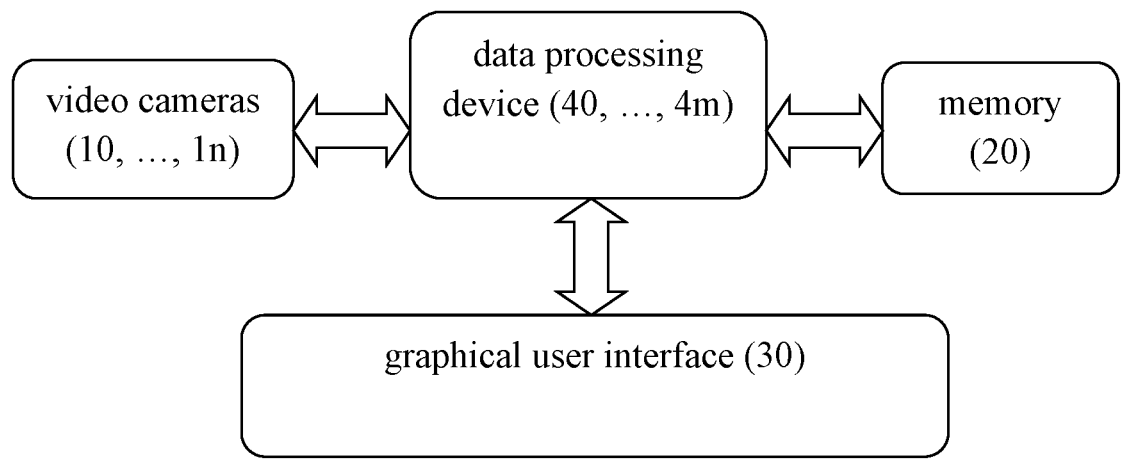
FIG. 1 is a block diagram of the system for detecting potentially dangerous situations.

FIG. 1 shows a block diagram of one of the embodiments of a computer system for detecting potentially dangerous situations. This system includes: at least one video camera (10, . . . , 1n); memory (20); graphical user interface (30); and at least one data processing device (40, . . . , 4m).

In the context of this application, computer systems are any systems based on hardware and software, such as: personal computers, smartphones, laptops, tablets, etc.

Memory devices may include, but are not limited to, hard disk drives (HDDs), flash memory, ROMs (read-only memory), solid state drives (SSDs), etc. In order to further understand the nature of the claimed solution, it is necessary to clarify that the system memory stores an archive of video data coming from all video cameras included in the security system. The memory offers the possibility to store data from all data processing devices.

The data processing device may be a processor, microprocessor, computer, PLC (programmable logic controller) or integrated circuit, configured to execute certain commands (instructions, programs) for data processing. The processor can be multi-core, for parallel data processing. In addition, a central processor, GPU, or other data processing devices, such as Intel NCS, FPGA cards, etc. may be used to analyze video data.

The graphical user interface (GUI) is a system of tools for user interaction with the computing device based on displaying all system objects and functions available to the user in the form of graphical screen components (windows, icons, menus, buttons, lists, etc.). Thus, the user has random access via data input/output devices to all visible screen objects—interface units—which are displayed on the display/screen.

The data input/output device can be, but is not limited to, mouse, keyboard, touchpad, stylus, joystick, trackpad, etc.

It should be noted that this system may include any other devices known in the background of the invention, such as input/output devices, graphics cards (including GPUs), various sensors, etc.

An example of the above-mentioned system for detecting potentially dangerous situations will be described below.

Let's consider a video surveillance system of a bank as an example. The entire perimeter of the premise (including individual rooms, if any) is equipped with video surveillance cameras. The video cameras are located in such a way that their fields of view are slightly intersected/overlapped. This is necessary to ensure there are no blind areas of the video surveillance system and, if necessary, to create (restore) a full picture of the event based on the video data.

Video data from each of the system's video cameras mentioned are sent in real time to at least one data processing device of the claimed system. In addition, this source video data is sent to the memory of the system for storing the archive. In the process of uploading to memory, in specific embodiments of the system, video data can be analyzed to form metadata that characterizes data about all objects in the video. In this case, metadata is detailed information about all objects moving in the field of view of each camera (motion trajectories, facial descriptors, etc.). The resulting metadata is also stored in the system memory. Subsequently, the resulting metadata can be used to perform a search based on the set criteria.

The data processing device analyzes the resulting video data to detect (identify) at least one human in the frame. Thus, it should be mentioned that several persons can be detected in the frame, as it is very rare that only one person is within the protected area. Each human is viewed separately from the others. That is, a data processing device analyzes each detected human individually and identifies key points of their skeleton. The key points characterize the main parts of the human body, the anatomical connection of which forms a human skeleton. In the simplest embodiment, the human skeleton has 17 key points characterizing, nose, eyes, ears, shoulders, elbows, hands, pelvis, knees, ankles. The more points, the more precise the skeleton will be defined; however, processing a large number of points will take a little longer. Each key point features its spatial coordinate.

After receiving the points, the user applies the graphical user interface (GUI) to set at least three corrective vertical lines (CVL) in the video frame in question. The mentioned CVL have a height equal to the average human height. A certain value of the average human height can be set at the system operation pre-setting stage. The system user sets the CVL parallel to the assumed back vector formed by the resulting key points of the skeleton. Thus, the mentioned CVLs are located on the same underlying plane as the human mentioned (on the floor, ground, etc.). Compliance with all the criteria listed enhances the accuracy of constructing the human skeleton vectors. To simplify user interaction with the system, the GUI is configured and set so that it is easy for the user to set the parallel lines, which are easy to place on the underlying plane.

Further, at least one data processing device calculates/receives horizontal lines (HL) for each of the specified CVL. In this field of technology, the mentioned HL is commonly referred to as "horizon lines". When receiving the HL, the following steps are performed:

the first vertical line is selected by passing through all set corrective vertical lines;

the second vertical line is selected by passing through all the lines remaining after selecting the first line by the set corrective vertical lines;

the equation of the line passing through the upper points of the selected vertical lines is formed;

the equation of the line passing through the lower points of the selected vertical lines is formed;

the point of intersection of the mentioned lines is calculated by solving the system of the resulting linear algebraic equations (SLAE);

the steps (b)-(d) are repeated to get a set of points;

the optimal points from the resulting set of points are selected by applying the RANSAC parameter estimation algorithm;

a horizontal line for the first corrective vertical line is constructed based on the resulting optimal points;

the steps (a) to (h) are repeated to obtain horizontal lines for each of the set corrective vertical lines.

Thus, a HL is constructed for each CVL and is stored for further application when obtaining a vector characterizing a human in a standing position.

Further, the data processing device automatically splits the frame into zones based on the preset CVL. Delaunay triangulation method is used for splitting (the inverse problem is the Voronoi diagram). This is necessary for determination of the corrective vertical lines that are closest to the human.

After splitting the frame into zones, at least one leg vector is constructed. To do this, a pair of lower limb key points is used. In the context of this application, a leg vector is a vector from the middle of the thighs to the middle of the lower limbs points (that is, the knees points or the ankles points). Thus, when the leg vector is constructed, the middle of the hip is considered as one key point, implying a point between the key points of the hip, and either the point of the ankle or the point of the knee is considered as the second key point, whereby the mentioned points also imply the middle between the key points of the same name.

Next, the zone with the mentioned pair of key points and hence the resulting leg vector is determined.

The back vector is constructed based on the CVL forming the above-mentioned zone and based on the previously obtained HL. In the context of this application, a back vector is a vector that characterizes a human in a standing position at a given (defined) point. It should be noted that the previously mentioned assumed back vector is less accurate than the resulting back vector at this stage.

Once the basic vectors (leg vector and back vector) are obtained, the data processing device determines the angle between them. The resulting angle is the tilt angle of the lower limbs. This angle is essentially the angle of deviation of the human's legs from the normal standing position. Based on the comparison of the value of this angle with the preset threshold (first), a human's posture is determined. For example, if the lower limbs tilt angle exceeds the threshold, the human is considered to be either in a sitting or lying position. If the lower limbs tilt angle is less than the threshold, the human is considered to be in a standing position. However, it should be mentioned that not all standing positions are considered a characteristic of the potentially dangerous situation, as will be explained in more detail below.

The final stage is to detect/identify a potentially dangerous situation if a human's posture is one of the postures indicating a potentially dangerous situation.

In the context of the claimed solution, four major postures that characterize a potentially dangerous situation are considered.

Sitting human in the frame. This human posture can characterize the presence of a hostage in the frame. Thus, the posture of the sitting human in the frame can characterize either a person sitting on a chair, a person sitting on a floor, or a person on their hunkers. Any of these postures will be considered a characteristic of a potentially dangerous situation.

Lying human in the frame. This posture can characterize the presence of a potentially injured person (injured person, hostage) in the frame or the presence of an attacker in the frame who has commanded everyone to lie down.

The human in the frame has at least one arm outstretched forward. This posture may characterize the potential presence of firearms in a person's hand.

The human in the frame has one or both hands raised up. This posture can characterize the presence of a hostage in the frame.

Let's consider the case when the lower limbs tilt angle is less than the preset threshold in more detail. In this case, the human may be either in a standing position or in a lying position in the direction to the camera. To exclude the lying position in the direction towards the camera, the following condition is verified. First, the length of the segment (l) connecting the point of the middle of the lower limbs with the projection of the neck point onto the back vector is determined. If the length ratio of this segment (l) to human height (h) exceeds the preset second threshold, the human in the frame is considered to be in the lying posture in the direction to the camera. That is, two conditions should be met for this posture to be determined.

It should be noted that the posture of the lying person in the frame is determined in another way, by constructing another new vector. Namely: a new vector of the back is constructed based on the key point of the neck and the key point of the hips. If the value of deviation angle of this new back vector from the previously mentioned back vector exceeds the preset third threshold, then the person is in the lying posture in the frame. Construction of this new back vector is only necessary if, for some reasons, it is impossible to construct a leg vector, for example, due to impossibility to determine the points of knees and points of the ankles in the frame. This can happen if the bottom of the detected human is obstructed, for example, by a table.

As for the standing position, after eliminating all possible lying positions, the system determines that the person is in the standing position if the value of the lower limbs deviation angle is less than the preset (first) threshold value.

At least one additional arm vector should be constructed based on a pair of the upper limbs key points in order to identify the potentially dangerous situation associated with this position. To achieve greater accuracy, two vectors (for the left and for the right arm respectively) are constructed. Next, the angle of deviation of the upper limbs, characterizing the angle of tilt of the arm vector from the back vector, is determined. If the arm vector is perpendicular to the back vector (that is, an angle of approximately 90 degrees), the human is considered to be in a position with at least one arm outstretched forward. If the two arms are perpendicular to the back vector, the human is considered to be in a position with two arms outstretched forward. Basically, both one and two arms outstretched forward characterize a potentially dangerous situation, so that it is enough to determine that one arm is perpendicular to the back vector.

If the arm vector is parallel to the back vector and the key point of the hand is higher than the key point of the shoulder, the human is considered to be in a position with at least one hand raised. It is possible to similarly determine whether only one hand or both hands are raised, if necessary (one raised hand is also enough to determine a potentially dangerous situation).

It should be noted that for improved accuracy of determining a human's posture in the frame and thus improved efficiency of the system as a whole, the graphical user interface is designed to give the user the ability to adjust the frame perspective before beginning to work with the system.

Besides, in order to exclude false actuation of the security system, the GUI is designed to provide the user with the ability to set and adjust the time interval during which a human's posture indicating a potentially dangerous situation is maintained. It is preferable to perform this adjustment at the stage of configuration before starting the system (however, if necessary and depending on the situation this time parameter can be also adjusted during the system operation). Thus, it is possible to exclude the situations, when a person crouches to tie a shoelace or when a person raises the hand to greet another person, etc. In this embodiment, a potentially dangerous situation is identified if a human's posture indicating a potentially dangerous situation is observed in the video data within a preset period of time.

It should be mentioned that, when a potentially dangerous situation is detected by any of the methods described above, at least one data processing device automatically performs one or several actions preset by the user.

Such actions include: recording video data to the archive, exporting a frame or a video, initiating an alarm, notifying the user with SMS, notifying the user by email, notifying the user with audio. Notification of the user may also be performed to exclude false actuation. For example, the system detected a potentially dangerous situation, automatically sent the video data to the system user/operator, so that the operator would view it and decide whether to initiate an alarm should be actuated or whether this is a false actuation.

It should be mentioned that the minimum list of the essential automatic actions is considered. Depending on the situation and requirements of various security systems, the claimed system can be configured to automatically perform any other action, such as switching to preinstalled rotary video camera, switching motion sensors or detectors on and off, running a software preset by the user, and many other actions that may be necessary if a potentially dangerous situation is detected in a protected area.

Below we will consider implementation of the method for detecting potentially dangerous situations in more detail.

Figure 2:
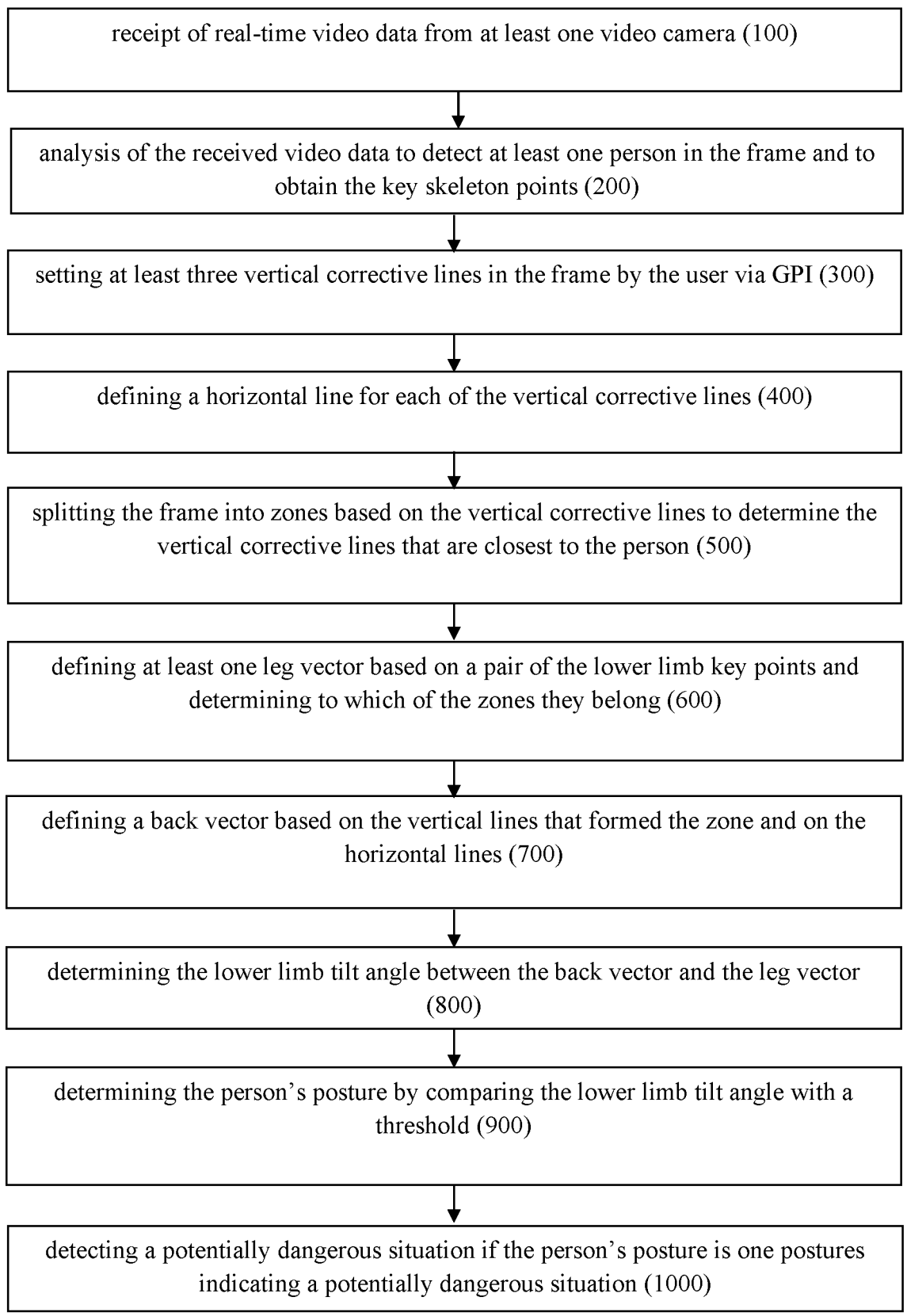
FIG. 2 is a block diagram of one of the embodiments of the method for detecting potentially dangerous situations.

FIG. 2 shows a block diagram of one of the embodiments of the method for detecting potentially dangerous situations. This method is implemented by at least one data processing device. Thus, the method contains the stages at which the following operations are executed:

(100) real-time video data is received from at least one video camera;

(200) the received video data is analyzed to detect at least one human in the frame and to obtain the key points of their skeleton, (300) thus, after receiving the key points, the user sets at least three corrective vertical lines in the frame with the height equal to the average human height and parallel to the assumed back vector formed by the resulting key points using the GPI, whereby the mentioned vertical lines are located on the same underlying plane as the human mentioned;

(400) the horizontal lines for each of the set corrective vertical lines are constructed;

(500) the frame is split into zones based on the set corrective vertical lines to determine the corrective vertical lines that are the closest to the human;

(600) at least one leg vector is constructed based on a pair of the lower limbs key points and their belonging to one of the resulting zones is determined;

(700) the back vector is constructed on the basis of the vertical lines that formed the resulting zone and on the basis of the horizontal lines;

(800) the lower limbs tilt angle between the resulting back vector and the leg vector is determined;

(900) a human's posture is determined by comparing the resulting lower limbs tilt angle with a preset threshold;

(1000) a potentially dangerous situation is identified, if a human's posture is one of the postures indicating a potentially dangerous situation.

It should be noted that this method is preferred to be implemented by means of the above-mentioned system for detecting potentially dangerous situations and, therefore, can be expanded and refined by all particular versions that were described above for embodiment of the system for detecting potentially dangerous situations.

Besides, the embodiment options of this group of inventions can be implemented with the use of software, hardware, software logic, or their combination. In this embodiment example, software logic, software, or a set of instructions are stored on one or multiple various conventional computer-readable data carriers.

In the context of this description, a "computer-readable data carrier" may be any environment or medium that can contain, store, transmit, distribute, or transport the instructions (commands) for their application (execution) by a computer device, such as a personal computer. Thus, a data carrier may be an energy-dependent or energy-independent machine-readable data carrier.

If necessary, at least some part of the various operations presented in the description of this solution can be performed in an order differing from the described one and/or simultaneously with each other.

Although the technical solution has been described in detail to illustrate the most currently required and preferred embodiments, it should be understood that the invention is not limited to the embodiments disclosed and, moreover, is intended to modify and combine various other features of the embodiments described. For example, it should be understood that this invention implies that, to the possible extent, one or more features of any embodiment option may be combined with one or more other features of any other embodiment option.

The invention claimed is:

1. A system for detecting potentially dangerous situations containing:
   a video camera;
   a memory storing video data;
   a graphical user interface (GUI);
   at least one a data processing device configured to:
     receive real-time video data from the video camera;
     analyze the video data to detect a human in a frame in the video data and to obtain key points of a skeleton of the human,
       wherein the GUI is configured to allow a user to define three corrective vertical lines in the frame,
       wherein the corrective vertical lines are an average human height in length,
       wherein the corrective vertical lines are parallel to an assumptive spine vector defined by the key points,
       wherein the human is positioned on an underlying plane, and
       wherein the corrective vertical lines are positioned on the underlying plane;
   determine horizon lines for each of the corrective vertical lines;
   split the frame into zones based on the corrective vertical lines to determine closest corrective vertical lines to the human;

determine a leg vector based on a pair of lower limb key points determined to belong to one of the zones;

determine a precise spine vector using the closest corrective vertical lines and the horizon lines;

determine a lower limbs tilt angle between the precise spine vector and the leg vector;

determine a human posture by comparing the lower limbs tilt angle with a preset lower limbs tilt angle threshold; and detect a potentially dangerous situation, if the human posture is one of postures indicating a potentially dangerous situation.

2. The system according to claim 1, wherein the following stages are performed for corrective vertical lines:
(a) selecting a first vertical line;
(b) selecting a second vertical line is from corrective vertical lines excluding the first vertical line;
(c) determining an upper line passing through upper points of the selected vertical lines;
(d) determining a lower line passing through the lower points of the selected vertical lines;
(e) determining an intersection point of the upper and lower lines by solving a system of linear equations;
(f) obtaining a set of intersection points by repeating the steps (b)-(d);
(g) selecting optimal points from the set of intersection points by using a RANSAC parameter estimation algorithm;
(h) constructing a horizon line for the first corrective vertical line based on optimal points;
(i) repeating the steps (a) to (h) to obtain horizontal lines for each of the corrective vertical lines.

3. The system according to claim 1, wherein the frame is split into zones by using Delaunay triangulation method based on location of the corrective vertical lines in the frame.

4. The system according to claim 1, wherein the leg vector is constructed, the middle of the hip is considered as one key point, implying a point between the key points of the hip, and either the point of the ankle or the point of the knee is considered as the second key point, whereby the mentioned points also imply the middle between the key points of the same name.

5. The system according to claim 4, wherein the human's posture indicating a potentially dangerous situation is one of the postures that characterizes: a sitting human in a frame, a lying human in a frame, a human with at least one arm outstretched forward, a human with at least one arm raised.

6. The system according to claim 5, wherein the posture of the sitting human in the frame characterizes the person sitting either on the chair, on the floor, or their hunkers.

7. The system according to claim 5, if the mentioned lower limbs tilt angle exceeds the preset threshold, the human in the frame is considered to be either in a sitting or lying posture.

8. The system according to claim 5, if the mentioned lower limbs tilt angle is less than the preset threshold value, whereby if the length ratio of the segment connecting the point of the middle of the lower limbs with the projection of the neck point on the back vector to the human's height exceeds the preset second threshold, the human in the frame is considered to be in the lying posture in the direction of the camera.

9. The system according to claim 5, wherein a new back vector is constructed based on the key point of the neck and the key point of the hips, whereby, if the tilt angle of this new back vector from the previously mentioned back vector exceeds the preset third threshold, then the human is in the lying posture in the frame.

10. The system according to claim 5, wherein the at least one arm vector is constructed based on a pair of key points of the upper limbs, whereby, if the arm vector is perpendicular to the back vector, the human is considered to be in a posture with at least one arm outstretched forward.

11. The system according to claim 5, wherein the at least one arm vector is constructed based on a pair of the upper limbs key points, whereby, if the arm vector is parallel to the back vector, and the hand key point is higher than the shoulder key point, the human is considered to be in a position with at least one hand raised.

12. The system according to claim 5, wherein a potentially dangerous situation is identified if a human's posture indicating a potentially dangerous situation is observed in the video data within a preset period of time.

13. The system according to claim 12, wherein the mentioned time is adjusted by the user when configuring the system operation.

14. The system according to claim 1, wherein the graphical user interface is configured to enable the user to adjust the frame perspective before starting operation of the system.

15. The system according to claim 5, wherein the data processing device automatically performs one or more actions preset by the user in case of detection of a potentially dangerous situation.

16. The system according to claim 15, wherein the actions include: recording video data to the archive, exporting a frame or a video, initiating an alarm, notifying the user with SMS, notifying the user by email, notifying the user with audio.

17. A method for detecting potentially dangerous situations implemented by at least one data processing device, whereby the method contains the stages at which the following operations are performed:

receiving real-time video data from a video camera;

analyzing the video data to detect a human in a frame in the video data and to obtain key points of a skeleton of the human,
wherein a graphical user interface (GUI) is configured to allow a user to define three corrective vertical lines in the frame,
wherein the corrective vertical lines are an average human height in length,
wherein the corrective vertical lines are parallel to an assumptive spine vector defined by the key points,
wherein the human is positioned on an underlying plane, and
wherein the corrective vertical lines are positioned on the underlying plane;

determine horizon lines for each of the corrective vertical lines;

split the frame into zones based on the corrective vertical lines to determine closest corrective vertical lines to the human;

determine a leg vector based on a pair of lower limb key points determined to belong to one of the zones;

determine a precise spine vector using the closest corrective vertical lines and the horizon lines;

determine a lower limbs tilt angle between the precise spine vector and the leg vector;

determine a human posture by comparing the lower limbs tilt angle with a preset lower limbs tilt angle threshold; and detect a potentially dangerous situation, if the human posture is one of postures indicating a potentially dangerous situation.

18. The method according to claim 17, wherein the following stages are performed for each of the set corrective vertical lines:
  (a) the first vertical line is selected by passing through all set corrective vertical lines;
  (b) the second vertical line is selected by passing through all the lines remaining after selecting the first line by the set corrective vertical lines;
  (c) the equation of the line passing through the upper points of the selected vertical lines is formed;
  (d) the equation of the line passing through the lower points of the selected vertical lines is formed;
  (e) the intersection point of the mentioned lines is calculated by solving system of linear equations;
  (f) the steps (b)-(d) are repeated to get a set of points;
  (g) the optimal points from the resulting set of points are selected by applying the RANSAC parameter estimation algorithm;
  (h) a horizontal line for the first corrective vertical line is constructed based on the resulting optimal points;
  (i) the steps (a) to (h) are repeated to obtain horizontal lines for each of the set corrective vertical lines.

19. The method according to claim 17, wherein the frame is split into zones by using Delaunay triangulation method based on location of the corrective vertical lines in the frame.

20. The method according to claim 17, wherein the leg vector is constructed, the middle of the hip is considered as one key point, implying a point between the key points of the hip, and either the point of the ankle or the point of the knee is considered as the second key point, whereby the mentioned points also imply the middle between the key points of the same name.

21. The method according to claim 20, wherein the human's posture indicating a potentially dangerous situation is one of the postures that characterizes: a sitting human in a frame, a lying human in a frame, a human with at least one arm outstretched forward, a human with at least one arm raised.

22. The method according to claim 21, wherein the posture of the sitting human in the frame characterizes the person sitting either on the chair, on the floor, or their hunkers.

23. The method according to claim 21, if the mentioned lower limbs tilt angle exceeds the preset threshold, the human in the frame is considered to be either in a sitting or lying posture.

24. The method according to claim 21, if the mentioned lower limbs tilt angle is less than the preset threshold value, whereby if the length ratio of the segment connecting the point of the middle of the lower limbs with the projection of the neck point on the back vector to the human's height exceeds the preset second threshold, the human in the frame is considered to be in the lying posture in the direction of the camera.

25. The method according to claim 21, wherein a new back vector is constructed based on the key point of the neck and the key point of the hips, whereby, if the tilt angle of this new back vector from the previously mentioned back vector exceeds the preset third threshold, then the human is in the lying posture in the frame.

26. The method according to claim 21, wherein the at least one arm vector is constructed based on a pair of key points of the upper limbs, whereby, if the arm vector is perpendicular to the back vector, the human is considered to be in a posture with at least one arm outstretched forward.

27. The method according to claim 21, wherein the at least one arm vector is constructed based on a pair of the upper limbs key points, whereby, if the arm vector is parallel to the back vector, and the hand key point is higher than the shoulder key point, the human is considered to be in a position with at least one hand raised.

28. The method according to claim 21, wherein a potentially dangerous situation is identified if a human's posture indicating a potentially dangerous situation is observed in the video data within a preset period of time.

29. The method according to claim 28, wherein the mentioned period of time is adjusted by the user when configuring the system operation.

30. The method according to claim 17, wherein the user can adjust the frame perspective before starting operation of the system using the GUI.

31. The method according to claim 21, wherein the data processing device automatically performs one or more actions preset by the user in case of detection of a potentially dangerous situation.

32. The method according to claim 31, wherein the actions include: recording video data to the archive, exporting a frame or a video, initiating an alarm, notifying the user with SMS, notifying the user by email, notifying the user with audio.

33. A non-transitory computer-readable data carrier containing instructions executed by at least one computer processor to implement the methods for detecting potentially dangerous situations according to claim 17.

* * * * *